United States Patent [19]

Boguslawski et al.

[11] 4,429,044

[45] Jan. 31, 1984

[54] PREPARATION OF AN ALKALINE PROTEASE FROM FLAVOBACTERIUM ARBORESCENS

[75] Inventors: George Boguslawski; Ernest W. Boyer, both of Elkhart, Ind.

[73] Assignee: Miles Laboratories, Inc., Elkhart, Ind.

[21] Appl. No.: 425,713

[22] Filed: Sep. 28, 1982

[51] Int. Cl.$^3$ ............................ C12N 9/52; C12R 1/20
[52] U.S. Cl. ...................................... 435/220; 435/850
[58] Field of Search ............................ 435/220, 850

[56] References Cited

U.S. PATENT DOCUMENTS 4,061,539 12/1977 Lee .......................................... 195/31
4,283,496 4/1981 Lee .......................................... 435/253

FOREIGN PATENT DOCUMENTS 55-127988 10/1980 Japan .................................... 435/850

OTHER PUBLICATIONS

Matsubara et al., P. D. Boyer Ed. The Enzymes, 3rd Ed., vol. 3, Acad. Press, New York, 1971, pp. 792–794.
Boguslawski et al., A Method for the Assay of Glucose Isomerase Activity in Complex Fermentation Mixtures, J. of Applied Biochemistry, 2, 367–372 (1980).
Muir et al. in Chemical Abstracts, vol. 90 (p. 452) 166676h (Abstract of J. Soc. Dairy Technol. 197932, 19–23).

*Primary Examiner*—Lionel M. Shapiro
*Attorney, Agent, or Firm*—Jerome L. Jeffers

[57] ABSTRACT

The production of an alkaline serine protease by a soil bacterium, *Flavobacterium arborescens* is disclosed. Also disclosed is the use of the protease as an enzyme detergent.

8 Claims, No Drawings

PREPARATION OF AN ALKALINE PROTEASE FROM FLAVOBACTERIUM ARBORESCENS

BACKGROUND OF THE INVENTION

Microbial proteases are of considerable interest for both theoretical and practical reasons. The proteases are often extracellular and can be isolated in active form from a spent culture filtrate.

The proteolytic enzymes are generally divided into four groups on the basis of their pH optima, sensitivity to diisopropylphosphofluoridate (DFP) and thiol reagents, and dependence on metals for activity. Thus, one distinguishes:

1 Acid proteases;
2 DFP-sensitive proteases (serine alkaline proteases);
3 metal chelator-sensitive proteases;
4 thiol proteases.

The first group includes such enzymes as microbial rennins and has a value in dairy industry for milk clotting and cheese ripening. The acid proteases are mostly of fungal origin.

The second group, into which the presently described protease falls, comprises the largest number of known proteases and shows the widest taxonomic distribution. Best characterized are the extracellular subtilisins produced by Bacillus sp. and several other enzymes elaborated by Gram-positive bacteria (e.g., Streptomyces, Arthrobacter) and fungi (e.g., Aspergillus, Saccharomyces). Detergent enzymes are the major industrial use for these proteases. Surprisingly, only a very few Gram-negative bacteria have been found to produce proteases of this category. These are disclosed by Matsubara et al. in P. D. Boyer, Ed. The Enzymes, 3rd Edition, Vol. 3, Pp 721–795, Acad. Press, New York, 1971. Pages 792–794 of this reference are particularly pertinent.

The metal chelator-sensitive proteases form a group of the so-called neutral proteases. These enzymes usually depend on zinc and calcium for activity and stability. Some of the proteases of this group are of use in the beer industry.

The smallest group of proteolytic enzymes of microbial origin is that of thiol proteases. Only a few such proteases have been characterized, e.g., thiol proteases for *Streptococcus lactis* and *Clostridium histolyticum*. There is no known industrial application for these enzymes.

The present invention is based on the isolation, characterization and use of an extracellular alkaline serine protease from a soil microorganism, *Flavobacterium arborescens*. The use of this organism for the production of another enzyme, glucose isomerase, is disclosed and claimed by C. K. Lee in U.S. Pat. No. 4,061,539. Two strains of *F. arborescens* which are disclosed in this patent as being suitable for the production of glucose isomerase, i.e., NRRL B-11,022 and ATCC 4358, were found to be well suited for the production of protease. The '539 patent does not indicate that an organism of this species is useful in the production of microbial alkaline protease.

SUMMARY OF THE INVENTION

The present invention is a method for the production of a microbial alkaline protease. The method involves cultivating the organism from the species *Flavobacterium arborescens* in an aqueous nutrient medium containing appropriate nutrients for a time sufficient to produce a recoverable quantity of enzyme.

DETAILED DESCRIPTION

A variety of growth media can be used for nurturing the *F. arborescens* during its production of protease. For example, an aqueous fermentation medium may contain 0.05 to 0.2% yeast extract, 0.5 to 2.0% xylose, 5 to 10% corn steep liquor and 0.5 to 1.0% potassium phosphate all on a weight/volume (w/v) basis. The pH is preferably adjusted to a level of from about 6.8 to 7.2.

Other fermentation media which could be used include 1% yeast extract or a nutrient broth with or without a carbon source. Typically, cells are grown in the medium of choice at a temperature of 29° to 32° C. for a period of from 16 to 24 hours, usually with agitation. After fermentation, the cells are removed, such as by centrifugation, to leave a clear supernatant containing the protease which may be recovered by methods of purification well known in the art. For example, the protease can be purified to homogeneity by addition of ammonium sulfate, precipitation and concentration followed by ion exchange chromatography on diethylaminoethyl (DEAE) cellulose and sucrose gradient centrifugation. Yields in the range of 4,000 to 16,000 units per liter are obtained with one unit being equivalent to that amount of enzyme which liberates 10 nanomoles tyrosine per minute at 50° C. and pH 9.0 with casein as a substrate.

Proteolytic activity is assayed in a total volume of 2.6 ml. The reaction mixture consists of 2 ml. of 0.7% (w/v) casein in 0.05 M Tris (hydroxymethyl) amino methane-HCl buffer, pH 9.0, using the enzyme and the buffer to make up the volume. The reaction is terminated by adding equal volumes of 1.8% (w/v) trichloroacetic acid and removing precipitated protein by centrifugation. The activity is measured as tyrosine released into the soluble fraction. The amount of tyrosine is calculated from the difference in absorbance at 275 nm between the reaction and the blank (reaction killed at time zero).

The enzyme produced by *F. arborescens* has a molecular weight of 19,000 and consists of a single polypeptide chain as determined by polyacrylamide gel electrophoresis under denaturing conditions.

The method of practicing the present invention is further illustrated by the following examples:

EXAMPLE 1

Microbial alkaline protease was prepared by the following procedure:

A separate inoculum of both *F. arborescens* NRRL B-11,022 and ATCC 4358 were grown in 1% (w/v) yeast extract in distilled water. In each case, the cells were introduced to 50 ml. of a fermentation medium consisting, on a weight/volume basis of 0.15% yeast extract, 0.5% potassium phosphate, 7.0% corn steep liquor and 1% xylose in distilled water. The fermentation broth, which had an initial cell density of $2 \times 10^7$ cells/ml. and a pH of 7.0, was allowed to incubate for 24 hours at 30° C. in a 300 ml. flask placed on a 250-rpm shaker with 1-inch eccentricity. After the 24 hour fermentation period, the cells were removed by centrifugation (5 minutes at 10,000×g) and the clear supernatant retained as the crude protease fraction with the co-produced glucose isomerase being retained in the cells.

EXAMPLE 2

The protease prepared in Example 1 from NRRL B-11,022 was purified using a five-step procedure as follows:

Purification of the protease

The spent growth medium (clear supernatant) from which the cells had been removed was designated as the crude enzyme (Fraction I). The proteins in this material were concentrated by precipitation with ammonium sulfate added to 70% saturation. The precipitate was collected by centrifugation for 30 minutes at 23,000×g, washed once with 70% saturated solution of ammonium sulfate (pH 7.4), and dissolved in 0.05 M Tris-HCl buffer, pH 8.0, containing 0.02 M NaCl. The very dark brown protein solution was dialysed overnight against the same buffer without NaCl and centrifuged at 40,000×g for 30 minutes to remove residual amounts of undissolved substances. The dialysed material (Fraction II) was applied to a DEAE-cellulose column equilibrated with 0.02 M NaCl in the above buffer. The column was washed with the equilibrating buffer until the $A_{280}$ of the eluate was near zero, and developed with a gradient of NaCl (0.02–1.00 M) in 0.05 M Tris-HCl buffer, pH 8.0. Most of the active material did not adsorb and was eluted as a light brown solution with the equilibrating buffer. The eluted enzyme was concentrated in an Amicon ultrafiltration unit using a UM-10 membrane (10,000 molecular weight exclusion). This was designated as Fraction III.

The DEAE-cellulose step was repeated with Fraction III to yield Fraction IV (still light brown). This was applied to a column of hydroxylapatite equilibrated with 0.01 M potassium phosphate buffer, pH 7.0. Again, most of the active enzyme was eluted with the equilibrating buffer, but the brown impurities were nearly completely retained on the column. The pale yellowish solution of the protease (Fraction V) was concentrated by ultrafiltration and applied to a 5–30% (w/v) gradient (36 ml.) of sucrose in 0.05 M Tris-HCl buffer, pH 8.0, containing 0.25 M NaCl. The gradient was centrifuged for 70 hrs. at 28,000 rpm in a Beckman SW28 rotor. The fractions with a constant specific activity were combined (Fraction VI), sterilized by filtration, and stored at 4° C.

Electrophoresis under denaturing conditions revealed the presence of a single protein band with the molecular weight of 19,050. This value agrees very well with the molecular weight of 19,400 calculated by comparison to the sedimentation rate of chymotrypsinogen (25,000) and ovalbumin (43,000) marker proteins run in a parallel sucrose gradient.

Proteolytic activity was determined as previously described before any purification and after each step of the purification process. The results of this experiment are set out in Table I.

TABLE I

| | Purification of *F. arborescens* protease | | | |
|---|---|---|---|---|
| Fraction | Specific Activity (units/mg protein) | Total units | Purification (-fold) | Yield (%) |
| I Crude Supernatant | 31.2 | 129,800 | 1.00 | 100.0 |
| II Ammonium Sulfate | 26.0 | 109,900 | 0.83 | 84.6 |
| III 1st DEAE-cellulose | 634.0 | 66,100 | 20.33 | 50.8 |
| IV 2nd DEAE-cellulose | 809.0 | 65,100 | 25.90 | 50.1 |
| V Hydroxylapatite | 1063.0 | 57,800 | 33.90 | 44.2 |
| VI Sucrose gradient | 1883.0 | 29,996 | 60.35 | 23.0 |

Table I indicates that the protease can be purified in a few simple steps with acceptable yields.

EXAMPLE 3

This experiment was carried out in order to determine the activity and stability of *F. arborescens* protease as a function of temperature.

Protease activity was measured at the indicated temperature. Stability was tested by heating the enzyme at a given temperature for 15 or 30 min., followed by assays at 37° C. Fraction VI (Table I) was used. The results of this experiment are set out in Table II.

TABLE II

| Temperature (°C.) | Activity (units) | Stability (% maximum) | |
|---|---|---|---|
| | | 15 min. | 30 min. |
| 30 | 1.16 | 100.0 | 100.0 |
| 37 | 1.78 | 100.0 | 100.0 |
| 42 | 2.24 | 94.1 | 88.2 |
| 50 | 2.55 | 33.3 | 11.8 |
| 55 | 2.59 | 0.0 | 0.0 |
| 60 | 2.56 | 0.0 | 0.0 |

EXAMPLE 4

The activity of *F. arborescens* protease as a function of pH and temperature was determined by the previously described procedure:

The results of this experiment are set out in Table III.

TABLE III

| Temperature (°C.) | pH[a] | Activity (% maximum) |
|---|---|---|
| 42 | 5.57 | 17 |
| | 5.84 | 23 |
| | 6.65 | 46 |
| | 7.60 | 70 |
| | 8.62 | 85 |
| | 9.62 | 93 |
| | 10.49 | 100 |
| | 11.37 | 5 |
| 50 | 7.47 | 86 |
| | 8.45 | 100 |
| | 8.88 | 97 |
| | 9.39 | 97 |
| | 9.94 | 85 |
| | 10.19 | 66 |
| | 11.01 | 6 |
| | 11.65 | 3 |

[a]measured at the temperature of the assay

Elevated temperature shifts the pH optimum toward lower values. The enzyme is active over a broad range of pH (5.5–10.5). Fraction VI (2.54 μg) was used in the assays.

EXAMPLE 5

An experiment was conducted to determine the effect of various inhibitors on the activity of *F. arborescens* protease. Fractions III and VI (Table I) were used as indicated in Table IV.

TABLE IV

| Enzyme Fraction | Inhibitor tested* | Activity (units) |
|---|---|---|
| III - 50 μg | — | 4.1 |
|  | 3.85mM EDTA | 4.1 |
|  | 1% (w/v) SSI | 1.6 |
| VI - 1.27 μg | — | 2.0 |
|  | 0.17mM DFP | 0.1 |
|  | 0.83mM PMSF | 1.9 |
|  | 83.00mM NEM | 2.0 |

*Abbreviations used:
EDTA = ethylenediamine tetraacetate
SSI = streptomyces subtilisin inhibitor
DFP = diisopropylphosphofluoridate
PMSF = phenylmethyl sulfonyl fluoride
NEM = N—ethyl maleimide The protease does not require metal ions for activity but is strongly inhibited by the subtilisin inhibitor and DFP. This behavior is typical of microbial alkaline proteases. Surprisingly, PMSF has no effect which is unusual because normally sensitivity to DFP and PMSF go together.

EXAMPLE 6

This example illustrates the effectiveness of *F. arborescens* alkaline protease as a laundry additive using Fraction I, Table I as the test enzyme.

The enzyme's stain-removing ability was measured on an Eidgenoessische-Material-Pruefungs-Anstalt (EMPA) (Federal Materials Testing Institute)-116 test fabric uniformly soiled with blood, milk, and Japanese ink (Test Fabrics, Inc., New York). The procedure used was the "Stain Removal Test" (Assay No. 35095, p. 99.1) available from the Technical Services Department of the Enzyme Products Division, Miles Laboratories, Inc., Elkhart, Indiana. This procedure is similar to that described by T. Coyle (J. Am. Oil Chem. Soc., 46, 515, 1969).

The stock detergent base was American Home Appliance Manufactures Association (AHAM) standard phosphate-containing detergent formulation. A Gardner XL-20 Tristimulus colorimeter (Gardner Laboratories, Inc., Bethesda, Md. was used for measurements, and the activity was measured as change in reflectance as a function of enzyme concentration, after appropriate corrections for blanks. The results are set out in Table V.

TABLE V

| Enzyme (units/l) | Reflectance Change |
|---|---|
| 1313 | 1.5 |
| 2625 | 2.5 |
| 5250 | 5.3 |

These results show that the increase in reflectance (stain removed) is directly proportional to the increase in concentration of alkaline protease in the test system.

EXAMPLE 7

The co-production of protease and glucose isomerase by *F. arborescens* is illustrated by this example and Table VI.

TABLE VI

| Medium | Activity (units) | |
|---|---|---|
|  | Glucose Isomerase* | Alkaline Protease |
| Defined[a] | 1,924 | 520 |
| Complex[b] | 14,567 | 4700 |

[a]The medium contains:
0.2% xylose, 0.05% KH$_2$PO$_4$, 0.03% KOH,
0.02% MgSO$_4$, 0.001% FeSO$_4$, 0.05% (NH$_4$)$_2$SO$_4$,
0.05% casamino acids, vitamins and trace elements.
[b]The medium is described in Example 1 along with fermentation conditions (same for both media).
*One unit of glucose isomerase activity is defined as the amount of enzyme which converts 1 μmole of glucose into 1 μmole of fructose per min. under specified conditions. (G. Boguslawski and S. W. Bertch, J. Appl. Biochem., 2, 367–372, 1980).

In defined medium containing 0.2% glucose, the protease is not synthesized and glucose isomerase is depressed to about 50% of control level.

What is claimed is:

1. A method for the production of microbial alkaline protease which comprises cultivating an organism from the species *Flavobacterium arborescens* in an aqueous nutrient medium containing appropriate nutrients for a time sufficient to produce a recoverable quantity of enzyme.

2. The method of claim 1 wherein the nutrient medium contains 0.05 to 0.2% yeast extract, 0.5 to 2.0% xylose, 5 to 10% corn steep liquor and 0.5 to 1.0% potassium phosphate all on a weight/volume basis.

3. The method of claim 2 wherein the pH of the nutrient medium is adjusted to a level of from about 6.8 to 7.2.

4. The method of claim 1 wherein the organism is cultivated at a temperature of 29° to 32° C. for a period of from 16 to 24 hours.

5. The method of claim 1 wherein the protease producing organism is *F. arborescens* NRRL B-11,022.

6. The method of claim 1 wherein the protease producing organism is *F. arborescens* ATCC 4358.

7. The method of claim 1 wherein the organism cells are removed from the nutrient medium by centrifugation to leave a clear supernatant containing the protease.

8. The method of claim 7 wherein the protease is purified to homogeneity by addition of ammonium sulfate to the supernatant with precipitation and concentration followed by ion exchange chromatography on diethylaminoethyl-cellulose and sucrose gradient centrifugation.

* * * * *